United States Patent [19]

Silversides et al.

[11] Patent Number: 4,975,420

[45] Date of Patent: Dec. 4, 1990

[54] AGENTS AND PROCEDURES FOR PROVOKING AN IMMUNE RESPONSE TO GNRH AND IMMUNO STERILIZING MAMMALS

[75] Inventors: David W. Silversides, San Francisco, Calif.; Bruce D. Murphy, Saskatoon, Canada; Reuben J. Mapletoft, Sastatoon, Canada; Vikram Misra, Saskatoon, Canada; Anne F. Allen, Sastatoon, Canada

[73] Assignee: University of Saskatchewan, Saskatchewan, Canada

[21] Appl. No.: 103,489

[22] Filed: Sep. 30, 1987

[51] Int. Cl.$^5$ ............................................. A61K 37/38
[52] U.S. Cl. ...................................... 514/15; 424/88; 514/800; 530/313; 530/328
[58] Field of Search ............... 530/313, 322, 328, 806; 514/15, 800; 424/88

[56] References Cited

U.S. PATENT DOCUMENTS

| | | | |
|---|---|---|---|
| 3,963,691 | 6/1976 | Hoffman et al. | 530/313 |
| 4,218,439 | 8/1980 | Rivier et al. | 530/313 |
| 4,263,282 | 4/1981 | von der Ohe et al. | 530/313 |
| 4,302,386 | 11/1981 | Stevens | 530/322 |
| 4,608,251 | 8/1986 | Mia | 530/313 |
| 4,618,598 | 10/1986 | Conn | 530/313 |
| 4,639,512 | 1/1987 | Audibert et al. | 530/313 |
| 4,676,981 | 6/1987 | Silversides et al. | 424/85 |

FOREIGN PATENT DOCUMENTS

0111841  6/1984  European Pat. Off. .

OTHER PUBLICATIONS

Fraser et al., "Effect of Active Immunization to Luteinizing Hormone Releasing Hormone on Serum and Pituitary Gonadotropins, Testes and Accessory Sex Organs in the Male Rat" J. Endocr., vol. 63, pp. 399–406 (1974).
"Active Immunization Against LHRH in the Female" by I. A. Jeffcoate and B. J. Keeling, pp. 363–377 of Immunological Aspects of Reproduction in Mammals.
"Production and Characterization of an Antiserum to Synthetic Gonadotropin-Releasing Hormone" by Y. Koch et al., vol. 55, No. 3, of Biochemical and Biophysical Research Communications.
"A Method for Preparing Beta-hCG COOH Peptide-Carrier Conjugates of Predictable Composition" by A. C. J. Lee et al., pp. 749–756 of vol. 17 of Molecular Immunology by Pergamon Press, 1980.

*Primary Examiner*—Johnnie R. Brown
*Assistant Examiner*—T. Wessendorf
*Attorney, Agent, or Firm*—Joseph C. Gil; Lyndanne M. Whalen

[57] ABSTRACT

A technique has been developed to cause a mammal to generate antibodies which will bind to its native GnRH thus suppressing the mammal's fertility. The technique involves vaccinating a mammal with a novel conjugate of an immuno stimulating carrier and a novel GnRH analogue. The analogue is substantially identical to the natural GnRH which is common to all mammals except that one or more of the normally occurring amino acids of this decapeptide have been replaced by an amino acid with a more reactive side group. A favored technique is to utilize an analogue containing cysteine which, of course, has as a sulfhydryl side group. This analogue may then be conjugated to a large protein carrier using a heterobifunctional agent carrying a group reactive with carboxyl or amino groups and a group reactive with sulfhydryl groups. This conjugate then forms the immunogen base for a vaccine which may also contain art recognized adjuvants. The vaccine formulation is then administered in a manner which raises a substantial amount of antibodies which bind to native GnRH. Injection in a manner which provides a slow release to the circulatory system such as IP, IM or SC is favored.

9 Claims, No Drawings

AGENTS AND PROCEDURES FOR PROVOKING AN IMMUNE RESPONSE TO GNRH AND IMMUNO STERILIZING MAMMALS

BACKGROUND OF THE INVENTION

The use of antibodies to interfere with the normal function of gonadrotrophin releasing hormone (GnRH, also known as LHRH or lutenizing hormone releasing hormone) in mammals in stimulating the pituitary gland to release gonadotrophins is well known but has never been developed to a state of practical utility. This interference results in rendering the treated mammal infertile for various periods of time. The antibodies have been supplied by the treated mammal by active immunization or they have been supplied by passive immunization. The latter technique is of interest for short term sterilization and has been described in U.S. Pat. No. 4,676,981. However, foreign antibodies typically have a rather limited half life in the host mammal and then retreatment is necessary if the suppressed fertility condition is to be maintained.

Active immunization has generally been recognized as the more efficient route to longer term effects. However, GnRH is only a decapeptide so some measure is necessary to make it visible to the immune system of a mammal. Although some mixtures of GnRH with adjuvants or other materials have been able to provoke the production of appropriate antibodies the most widely used approach has been to couple the GnRH molecule to a large protein carrier molecule. A good review of this work appears in "Active immunization against LHRH in the female", a chapter by I. A. Jeffcoate and B. J. Keeling at pages 363 to 377 of *Immunological Aspects of Reproduction in Mammals* edited by D. G. Crighton and published by Butterworth's of London in 1984. This review discusses the use of various coupling agents including carbodiimide (1-ethyl-3-(3-dimethylaminopropyl)-carbodiimide), mixed anhydride, glutaraldehyde and bisdiazotized benzidene. Although the bis-diazotization coupling route involves a two step procedure such as is described in "Production and Characterization of an Antiserum to Synthetic Gonadotropin-Releasing Hormone" by Y. Koch et al in volume 55, number 3 (1973) of *Biochemical and Biophysical Research Communications* it is based on addition to the normally occurring side groups of the histidine or tyrosine residues.

The art has also recognized the value of using heterobifunctional coupling agents with haptens which have appropriate side groups. One approach was to use coupling agents carrying a group reactive with sulfhydryl groups and a group reactive with amino groups with haptens which carry sulfhydryl groups. In some cases haptens which do not carry such groups have been thiolated. A procedure of using such heterobifunctional agents is described in "A Method For Preparing beta-hCG COOH Peptide-Carrier Conjugates of Predictable Composition" by A. C. J. Lee et al at pages 749 to 756 of volume 17 of *Molecular Immunology* published by Pergamon Press of the U.K. in 1980. It involves a two step procedure of reacting a carrier protein which has many amino groups with the coupling agent (such as 6-maleimido caproic acyl N-hydroxy succinimide ester or MCS) and then reacting the so activated carrier with the sulfhydryl carrying peptide.

However, the art does not teach a technique of actively immunizing mammals against GnRH using commercially acceptable adjuvants. Most work done with the known GnRH-carrier conjugates has involved adjuvants such as Freunds' Complete or Incomplete Adjuvant which have limited utility outside the laboratory. This is believed to be due to the fact that the immunogenicity of these conjugates has been variable and to some extent not precisely controllable. This in turn is believed to arise from difficulties in developing a reproducible conjugation regimen.

The present invention involves the discovery of how to make the reproducible and controllable conjugation regimens available with heterobifunctional coupling agents available to GnRH carrier conjugates.

SUMMARY OF THE INVENTION

A class of readily produced agents have been developed which can be used in combination with practical vaccine adjuvants to cause a mammal to mount an immune response to its native GnRH thus suppressing the mammal's fertility comprising a conjugate of a GnRH analogue and an immuno stimulating carrier. The analogue is a GnRH molecule in which one or more of the ten naturally occurring amino acids has been replaced by an amino acid with a more reactive side chain. The carrier is any of those substances, especially large proteins, which are recognized in the field in immuno chemistry as making low molecular weight haptens visible to the immune system of mammals. The GnRH analogue is preferably one which carries a side chain with a reactive group with a reactivity substantially different from any group typically found to any significant extent on immunological carriers. The carrier is preferably a high molecular weight protein which has an established history as an immunogen.

Mammals may be rendered sterile for substantial periods of time by immunizing them with these conjugated agents. Typically these agents are introduced to the circulatory system of a mammal in combination with a recognized vaccine adjuvant.

DETAILED DESCRIPTION OF THE INVENTION

The GnRH analogue is the modification of the naturally occurring decapeptide in which one or more of the normal amino acids has been replaced with an amino acid with a side chain bearing a more reactive group. The natural molecule lacks any side chains bearing primary amino, carboxylic acid or sulfhydryl groups. In this regard, the pendant carboxylic acid group of the one position glutamic acid is not available for conjugation because it is cyclized with the alpha amino group of this amino acid to form a pyrrolidone ring. The analogues of the present invention do not involve simply opening this ring or synthesizing the natural GnRH with an uncyclized glutamic acid. The preferred reactive group is the sulfhydryl group because many carriers are available which do not carry many, if any, such reactive groups. It is particularly preferred to replace one of the naturally occurring amino acids with cysteine although the other S bearing amino acids, cystine or methionine, could be suitably modified to yield sulfhydryl groups. It is especially preferred to effect this replacement at the one, six or ten position of the GnRH.

The GnRH analogues can be synthesized by any of the well-known techniques for peptide synthesis. A particularly advantageous procedure is automated solid state peptide synthesis. Machines which effect such synthesis are available from DuPont and Cambridge Research Biochemicals of Cambridge, England.

The carrier may be any of those recognized in the field of immunology as making haptens visible to the immune system of mammals. Both GnRH and its more readily conjugated analogues with which the present invention is concerned are generally recognized as too small to act as immunogens; although antibodies will bind to them they are generally unable to provoke the generation of such antibodies. In the forty some years since the pioneering work of Landsteiner the technology of conjugating small molecules, known as haptens, to much larger carrier molecules has become well established. These carriers are typically proteins, and are preferable proteins which do not carry any substantial number of sulfhydryl groups. Suitable polypeptides preferably have molecular weights in excess of about 15,000 daltons. A preferred class of carriers are those able to provoke an immunological response as measured by antibody titer equal to or greater than that directed against the conjugated GnRH analogue. Suitable carriers include keyhole limpet hemocyanin, porcine thyroglobulin, bovine serum albumen, equine gamma globulin, horse albumen, ovalbumin and tetanus toxoid.

The conjugation agent used to link the GnRH analogue to the carrier molecule may be any agent which carries at least two reactive groups. These groups should be reactive with sites on both the carrier molecule and the GnRH analogue under conditions which do not adversely affect either the carrier or the GnRH analogue. Preferably, this agent carries at least two groups which have different reactivities and more preferably this agent carries at least two groups which are reactive with different partners. Especially preferred are heterobifunctional agents and most especially preferred are such agents carrying one group reactive with sulfhydryl groups and another group reactive with a common group on recognized carriers. These common groups include carboxylic acid and amino groups. An especially suitable conjugation agent is a heterobifunctional cross-linking agent carrying a group reactive with sulfhydryl groups and a group reactive with amino groups. Suitable agents include m-maleimido-benzoyl-N-hydroxysuccinimide ester, m-maleimido- benzoylsulfosuccinimide ester, N-succinimidyl-(4-idoacetyl) amino benzoate, succinimidyl-4-(N-maleimidomethyl)-cyclohexane-1-carboxylate, succinimidyl-4-(p-maleimidophenyl)butyrate, N-succinimidyl-3-(2-pyridyldithio)propionate, sulfosuccinimidyl-(4-idoacetyl)amino benzoate, sulfosuccinimidyl- 4-(N-male-imidomethyl)cyclohexane-1-carboxylate, N-succinimidylbromoacetate and sulfosuccinimidyl-4-(p-maleimido phenyl)butyrate. Particularly preferred heterobifunctional cross-linking agents are those carrying either a maleimide or a succinimidyl carboxylate group and agents carrying both groups are especially preferred. A full range of suitable agents is internationally available through the Pierce Chemical Company of Rockford, Ill., and this Company's publicly distributed General Catalog contains a disclosure of the structure and activity of suitable agents.

The GnRH analogue may be conjugated to the carrier at a wide range of ratios primarily limited by practical considerations. A conjugation ratio of less than 1:1 makes no practical sense since the unconjugated GnRH analogue is immunologically inactive; it does not function as an immunogen. High conjugation ratios tend to imperil the water solubility of the conJugate. Conjugation ratios of between about 2 and 16 GnRH analogues per $10^5$ daltons of carrier are preferred as being convenient but the immunological response does not appear to be substantially effected by the conjugation ratio.

The conjugation ratios actually obtained can be conveniently determined by incorporating a label into the GnRH analogue to be conJugated. The incorporation of carbon 14 into one of the amino acids, such as glycine, of the analogue has proved advantageous. After the conjugation procedure has been completed the unconjugated GnRH analogue can be readily separated from the carrier molecules, which are typically large proteins, by standard column chromatography techniques. One such technique which is preferred is molecular size fractionation. Typically a standard is used to establish the elution volumes or times representative of these large proteins. The carbon 14 activity of this separated protein material can then be used to determine the GnRH analogue content of the conjugates.

A particularly preferred conjugation technique involves a two step procedure involving a heterobifunctional conjugation agent reactive with amino groups and sulfhydryl groups and a GnRH analogue containing a cysteine residue. A particularly suitable class of such agents are those carrying both a maleimide group and a succinimidyl carboxylate group. This conjugation agent is reacted with an appropriate carrier molecule and then the unreacted agent is separated from the carrier by molecular size fractionation typically by standard column chromatography techniques. The GnRH analogue is then added to the activated carrier. It has been found particularly advantageous to add the GnRH analogue as a dry material. The coupling or conjugation efficiency using such a procedure has been found to be nearly one hundred percent.

The very high efficiency of this conjugation procedure facilitates obtaining reproducible results. Thus, once the conjugation ratio achieved by a particular precise protocol has been established it can be relied upon to give approximately the same ratio when subsequently repeated.

The reliability and efficacy of the conjugation using a cysteine replacement can be enhanced by ensuring that only the sulfhydryl group of the cysteine increases the reactivity of the GnRH analogue. Thus, if the cysteine replaces either the terminal amino acids which normally occur in GnRH the free amino or carboxyl group of the cysteine should be blocked. For instance, if replacement is at the one position, the free amino group can be derivitized by an N-acetyl group while if replacement is at the ten position, the free carboxyl group can be derivitized by amidation. Naturally, replacement at any other position such as the six position does not entail such a concern; both the amino and carboxyl groups of the cysteine are consumed in bonding into the peptide molecule.

The GnRH carrier conjugates may be combined with adjuvants to amplify their immunological effect. These conjugates are immunologically active even when administered in saline but like other immunogens their activity or effectiveness in stimulating antibody production in mammals can be enhanced by formulation with an adjuvant. Suitable adjuvants are any of those substances recognized by the art as enhancing the immunological response of a mammal to an immunogen without causing an unacceptable adverse reaction. For instance, Freund's complete adjuvant is a very effective enhancer but is not a suitable adjuvant because of the pain, abscess formation and fever associated with its use. The suitable adjuvants include aluminum compounds such as alhydrogel (an aluminum hydroxide gel), water-in-oil emulsions such as Freund's incomplete adjuvant and peanut or sesame oil emulsified with glycerol, muramyl dipeptides such as N-acetyl-muramyl-L-alanyl-D-glutamine-n-butylester in an appropriate vehicle such as squalene, liposomes, lipophilic quaternary compounds such as dimethyl dioctadecyl ammonium bromide, acrylic acid polymers such as Carbopol (acrylic acid cross-linked with allyl sucrose), monophosphoryl lipid A, and other materials which display a depot effect, i.e. gradually release the immunogen to the circulatory system of the mammal, and are reasonably well tolerated when administered parenterally. Suitable cross-linked acrylic acid adjuvants are taught in U.S. Pat. Nos. 3,919,411; 3,869,546: and 3,790,665. Reconstituted collagen based adjuvants are taught in U.S. Pat. No. 3,639,577. Particularly interesting adjuvants include alhydrogel, dimethyl dioctadecyl ammonium bromide, dextran sulphate, acrylic acid cross-linked oil, Liposomes, threonyl muramyl dipeptide in squalene, Esopher, Regressin alone and in oil, a combination of the cross-linked acrylic acid formulation with Liposomes and a combination of Regressin with Alhydrogel.

The formulation of the GnRH carrier conjugates with the adJuvants is in accordance with the normal recommendations for the adjuvant. In general, the conjugate is utilized in such formulations just as any other immunogen. The formulation may be enhanced by the addition of a further adjuvant or other enhancer. A classical definition of an adJuvant is a material which has a depot effect. Some of the materials discussed as adjuvants hereinabove do not provide such an extended period of release of the immunogen and might in this sense be considered enhancers. For instance, muramyl dipeptides amplify the response provoked by an immunogen but do not display a depot effect. Such enhancers are advantageously combined with materials which do display such a depot effect. In this regard, the muramyl dipeptides are advantageously combined with oils such as squalene or with Alhydrogel.

The antibody response is not sensitive to the precise dose administered. Positive results have been obtained with a dose as low as 10 micrograms of GnRH carrier conjugate. A significant immune response has been obtained with as little as 0.9 micrograms or 0.8 nano moles of GnRH analogue which was conjugated to an appropriate carrier. An appropriate dosage in smaller animals such as mice is between about 10 and 200 micrograms of conjugate while in the larger animals a range between about 100 and 700 micrograms of conjugate is preferred with a range between about 200 and 600 micrograms of conjugate being especially preferred The conjugate may be used to provoke an immune response in any mammal in which it is desired to obtain temporary sterility. It is preferred to use the conjugate to effect immuno sterilization in show animals, companion animals and food animals. It is especially preferred to utilize this technique with horses, dogs, cats, sheep and cattle.

The administration route of the conjugate is not critical. However, it is preferred to use a route which gradually releases the conjugate to the circulatory system and consequently the humoral immune system of the mammal. Thus, subcutaneous or intramuscular injection is preferred over intravenous injection. An administration route that involves passage through the gastrointestinal tract is not favored because of the very likely degradation of the conjugate and possible difficulties in absorption into the circulatory system.

The administration regimen is also not critical. However, it is preferred to delay the second and any subsequent administration sufficiently to obtain an increase in immune response over that obtained from the immediately previous administration. This response is conveniently measured by the titer of the treated animal's antibodies against GnRH. Thus, if this titer does not increase significantly after a booster administration but an immune response was observed after the initial administration booster was probably administered too soon to obtain the most advantageous result. Also, the administration of a booster before the response to the previous administration has fully developed may result in a less than optimal result. A primary injection followed by a booster approximately three weeks later has proven advantageous, as has a second booster after approximately a further three weeks.

The administration volume is not critical but is controlled by practical considerations. On the one hand, too high a volume may prove inconvenient or difficult to administer depending on the size and pacificity of the mammal being treated. On the other hand a minimum volume may be necessary to obtain the viscosities desired; some formulations such as those utilizing Freund's Complete Adjuvant require a minimum amount of dilution to achieve viscosities low enough to pass conveniently through a hypodermic needle. For small laboratory mammals such as the mouse or the rat an convenient while for the larger mammals such as cattle or sheep an administration volume around one milliliter is typical. For the intermediate size mammals such as the dog and cat a one milliliter administration volume at multiple sites per administration has been found suitable.

The immunological response provoked by administration of the GnRH carrier conjugate can be conveniently measured by antibody titer or physiological effect. Any of the well established techniques for determining the level of antibodies against a given antigen including radioimmuno assay (RIA) or enzyme linked immuno adsorbant assay (ELISA) may be employed. The use of RIA procedures based upon Iodine 125 has been found to be suitable. The radioactive tracer iodine can be readily bound to naturally occurring GnRH using a modified chloramine-T technique and the unbound iodine removed by affinity chromatography. This labelled GnRH can be used in liquid or solid primary binding assays or in competitive inhibition assays. A useful benchmark for such analysis is the titer or serum dilution at which the counts for radioactive iodine are 10 percent of the total counts available if all added tracer had bound to antibody.

It has been observed that effective carrier molecules typically provoke a stronger antibody response than the GnRH analogues to which they are conjugated. Normally, the titer of anti carrier antibody is at least about one order of magnitude higher (a response is detected at least one order of magnitude greater dilution) than that of the anti GnRH analogue antibody.

The physiological effect can be evaluated by a number of techniques including histology and sex hormone levels. Successful immunization with the GnRH analogue carrier conjugate may be detectable in the reduced weight or size of the treated mammal's testes or ovaries. A positive response may also be detectable in the reduced or suppressed function of these organs. For example in the male spermatogenesis in the testes of a treated mammal may be severely inhibited or entirely suppressed and the epididymis may be free of gametes and in the female ovulation may be suppressed. An additional indication may be a reduced level of testosterone or progesterone.

The invention is further illustrated, but is not intended to be limited by the following examples in which all parts and percentages are by weight unless otherwise specified.

EXAMPLES

Example 1

Production of a carrier/GnRH Analogue Conjugate

Three GnRH analogues were prepared by solid state peptide synthesis to have the same structure as naturally occurring GnRH except that the first, sixth or tenth normally occurring amino acid was replaced by cysteine and, in the case of terminal replacements, the free terminal group was inactivated. The analogue with replacement at the one position necessarily also involved loss of the pyrollidone group associated with the normally occurring glutamic acid and the analogue with replacement at the ten position did not initially have the amido group normally associated with the terminal glycine. In the former case the free amino group was N-acetylated and in the latter case the free carboxyl group was amidated. In the case of ten position replacement a carbon 14 label was incorporated into six position glycine and in the cases of the one and six replacements this label was incorporated into the ten position glycine.

The carrier molecules of keyhole limpet hemocyanin (KLH) were prepared for conjugation by activation with m-maleimido benzoyl sulfo succinimide ester (SMBS). Ten milligrams of carrier molecule was dissolved in two milliliters of a conJugation buffer obtained by combining 8.77 grams of NaCl, 13.8 grams of Na$_2$H PO$_4$ and 800 milliliters of distilled H$_2$O, adjusting the pH to 7.5 with one normal HCl and adjusting the volume to one liter with distilled H$_2$O. One and one quarter milligrams of dry SMBS was added to this solution, mixed gently, and allowed to react at room temperature for one hour. The excess SMBS was separated from the activated carrier by fractionation on a Sephadex G 25 PD-10 Pharmacia column with collection of the high molecular weight peak eluting at between 3 and 5.5 milliliters.

The conjugation was effected by adding this activated carrier solution to one milligram of dry GnRH analogue. In the case of the ten position replacement the analogue was first solubilized in 200 microliters of ethanol and then added to the carrier solution. In both cases the addition was followed by gentle mixing and a two hour reaction period at room temperature. The reaction bath was then fractionated on a PD-10 colmmn and the high molecular weight peak eluting between 3 and 6 milliliters was collected to effect a separation from any analogue which had not been conjugated.

The protein content of the conJugate was determined by Coomasie blue protein assay. A standard curve was generated from solutions of varying strength of bovine serum albumen (BSA) in the conjugation buffer by adding 200 microliters of Biorad protein reagent to 200 microliters of such solutions, vortexing briefly and reading the optical density at 595 nanometers. The conjugate solution volume was adjusted to 200 microliters and combined with 200 microliters of Biorad .1 protein reagent. Comparison of the optical density at 595 nanometers with the standard curve gave the protein content.

The GnRH analogue content of the conjugate was determined from the counts per minute (CPM) from the carbon 14 label. A 100 microliter sample was added to 5 milliliters of Aqua Sol scintillation cocktail from New England Nuclear and counted for one minute on a Beckman scintillation counter.

The conjugate was found to have an analogue to carrier ratio of 7.7 analogue units per $10^5$ daltons of carrier.

The conjugation efficiency was found to be nearly 100%. Instead of collecting and pooling the conjugate based on the six position replacement analogue which eluted at between 3 and 6 milliliters, one milliliter aliquots were collected over the entire practical elution range of the PD-10 column (1 to 18 milliliters). Each aliquot was analyzed for both protein content and analogue content by Coomasie blue protein assay and carbon 14 CPM, respectively. On appropriate adjustment of the scales the graphs of protein content and analogue content both against elution volume were superimposable. This indicated that the carrier protein and analogue now had the same elution pattern and thus were both part of the same molecule.

Example 2

Vaccination with a carrier/GnRH analogue

A conjugate prepared in accordance with Example 1 based on KLH and the six position replacement analogue with a conJugation ratio of 7.9 was used to treat 5 Balb/c mice. Each mammal was given an initial intraperitoneal injection of 50 micrograms of conjugate in 200 microliters of saline followed fourteen days later with a booster inJection of the same formulation and dose by the same route. At twenty-one days the mice were bled via infra orbital venipuncture and the serum was tested for anti GnRH antibodies by liquid phase primary binding assay. In particular, 100 microliters of the serum sample or an appropriate serial dilution was incubated at 4° C overnight with 100 microliters of Iodine 125 labelled GnRH displaying 20,000 CPM per 100 microliters in the presence of 100 microliters of PBS-gel solution. The protein bound radio labelled GnRH was isolated by precipitation with 1 milliliter of cold ethanol and centrifugation for ten minutes at 1200 g at 4° C. The decanted precipitate was evaluated in a Micromedic automated gamma counter. The results were calculated as the percent of total counts displayed by this decanted precipitate: an initial 300 microliter incubated sample contained 20,000 CPM so the CPM observed for the decanted precipitate of this sample would be divided by this number to give a percentage. A ten percent level was arbitrarily selected as the appropriate benchmark.

Three of the mice displayed at least 10 percent bound label at 10:1 serum dilution and two of the mice displayed at least 10% bound label at a 100:1 serum dilution. Thus, a significant immune response had been provoked by this conjugate.

Example 3

Vaccination with adjuvanted conjugates

The effect of conjugation ratio on immunological response for adjuvanted formulations of conjugates based on GnRH analogues with replacement at the one and six positions was determined. These conjugates were prepared in accordance with the procedures of Example 1 but using varying amounts of the analogues in the second step of the conjugation. The conjugation ratios for the one replacement were 3.5, 6.3 and 10.6 while the ratios for the six replacement were 3.7, 7.3 and 14.6, in each case to $10^5$ daltons of carrier, which was KLH.

The conjugates were combined with an adjuvant very similar to that taught by Example III of U.S. Pat. No. 3,919,411. Fifty micrograms of conjugate in phosphate buffered saline (PBS) was combined with an emulsion of about 2 weight percent Carbopol 934P (a polyacrylic acid crosslinked with polyallyl sucrose) in 50:45 by volume mixture of water and cotton seed oil which also contains 2.5 volume percent of sorbitan monolaurate and 2.5 volume percent of ethoxylated sorbitan monooleate (20 moles ethylene oxide). The formulation was made up of 9 volume parts conjugate solution to 1 volume part of emulsion.

Two hundred microliters of adjuvanted formulation was administered intraperitoneally to thirty Balb/c mice twice on a fourteen day interval. Each of the six conjugates (three conjugation ratios for each base GnRH analogue) was administered to five mice.

Essentially all thirty mice displayed antibody production against natural GnRH after 21 days. In particular, a 10:1 dilution of serum for every mouse had an Iodine 125 count of at least 10 percent of the total counts expected if all Iodine 125 labelled GnRH had been bindable and had been bound by antibody. The serum of sixteen mice met or exceeded this minimum at a 100:1 dilution and the serum of three did so at a 1000:1 dilution. There was no clear correlation between either GnRH analogue base or conjugation ratio and antibody production.

Example 4

Effect of Dose With An Adjuvanted Conjugate

The effect of four dose levels of an adJuvanted formulation based on a six position replacement analogue conjugated to KLH at a $7.7:10^5$ dalton ratio on antibody production was evaluated. Dosage levels of 10, 50, 100 and 200 micrograms of conjugate were utilized. Five Balb/c mice were given each dosage intraperitoneally in a 200 microliter injection on day zero and fourteen and the antibody production was evaluated on day 21. The formulation and adjuvant were the same as in Example 3 except that the conjugate content was varied.

The antibody response was evaluated in the same manner as in Examples 1 through 3 by the binding of a Iodine 125 labelled GnRH. No statistically significant difference between the four groups of five mice each was observed: all four dosage levels appeared to have provoked about the same response. All but one of the mice met the 10% of total counts bench mark at a 1:10 serum dilution, 9 of 20 met the benchmark at a 1:100 dilution and 4 of 20 still met the benchmark at a 1:1000 dilution.

Example 5

Effect of Carrier on Adjuvanted Formulations

Five conjugates were prepared using the six position replacement GnRH analogue and five different carriers. The conjugates were formulated and administered in the manner described in Example 3; they were combined with the polyacrylic acid based adjuvant and administered intraperitoneally in 200 microliter volumes and 50 microgram conjugate doses to 5 Balb/c mice per conjugate at days zero and fourteen. The antibody production provoked was evaluated at day 21 by the binding with Iodine 125 labelled GnRH as described in Example 2. The carrier, conjugation ratio per $10^5$ daltons of carrier and projected titer for ten percent of the total counts (as defined in Example 3) were recorded in Table 1. The projected titer is extrapolated from the results at dilutions of $10^{-1}$, $10^{-2}$, $10^{-3}$ and $10^{-4}$.

TABLE 1

| Animal # | Carrier | Conjugation Ratio | Projected Titer for 10% Total Counts |
|---|---|---|---|
| 1 | Porcine Thyroglobulin (IGB) | 8.3 | 50 |
| 2 | Porcine Thyroglobulin (IGB) | 8.3 | 65 |
| 3 | Porcine Thyroglobulin (IGB) | 8.3 | 68 |
| 4 | Porcine Thyroglobulin (IGB) | 8.3 | 38 |
| 5 | Porcine Thyroglobulin (IGB) | 8.3 | 22 |
| 6 | Bovine Serum Albumin (BSA) | 4.6 | 210 |
| 7 | Bovine Serum Albumin (BSA) | 4.6 | 1 |
| 8 | Bovine Serum Albumin (BSA) | 4.6 | 1 |
| 9 | Bovine Serum Albumin (BSA) | 4.6 | 1 |
| 10 | Bovine Serum Albumin (BSA) | 4.6 | 47 |
| 11 | Keyhole Limpet Hemocyanin (KLH) | 7.7 | 210 |
| 12 | Keyhole Limpet Hemocyanin (KLH) | 7.7 | 330 |
| 13 | Keyhole Limpet Hemocyanin (KLH) | 7.7 | 430 |
| 14 | Keyhole Limpet Hemocyanin (KLH) | 7.7 | 88 |
| 15 | Keyhole Limpet Hemocyanin (KLH) | 7.7 | 7000 |
| 16 | Equine Gamma Globulin (E.G.G.) | 15.4 | 560 |
| 17 | Equine Gamma Globulin (E.G.G.) | 15.4 | 14 |
| 18 | Equine Gamma Globulin (E.G.G.) | 15.4 | 135 |
| 19 | Equine Gamma Globulin (E.G.G.) | 15.4 | 95 |
| 20 | Equine Gamma Globulin (E.G.G.) | 15.4 | 165 |
| 21 | Tetanus Toxoid (T.T.) | 5.9 | 14 |
| 22 | Tetanus Toxoid (T.T.) | 5.9 | 1 |
| 23 | Tetanus Toxoid (T.T.) | 5.9 | 1 |
| 24 | Tetanus Toxoid (T.T.) | 5.9 | 1 |
| 25 | Tetanus Toxoid (T.T.) | 5.9 | 10 |

The EGG could be statistically grouped with either the KLH or with both the BSA and IGB by the Mann-Whitney test ($p<0.05$). The BSA and TT could be statistically grouped as giving inferior results than the other three carriers.

Example 6

Ten Balb/c mice were treated in accordance with the protocol of Example 3 with an adjuvanted formulation of a conjugate of one position replacement GnRH analogue and KLH with a conjugation ratio of 10.6 per $10^5$ daltons and the antibody response at day 7 and 21 was evaluated according to the assay described in Example 2. The formulation and adjuvant were as described in Example 3. The results were recorded in Table 2. The "Projected 10% Titer" is extrapolated from results at dilutions of $10^{-1}$, $10^{-2}$, $10^{-3}$ and $10^{-4}$.

TABLE 2

| Animal # | One Week Projected 10% Titer | Three Week Projected 10% Titer |
| --- | --- | --- |
| 1 | 1 | 1550 |
| 2 | 1 | 900 |
| 3 | 1 | 10 |
| 4 | 22 | 2150 |
| 5 | 35 | 4300 |
| 6 | 1 | 2650 |
| 7 | 70 | 2800 |
| 8 | 1 | 5100 |
| 9 | 1 | 1750 |
| 10 | 1 | 5800 |

Example 7

Vaccination of Cattle

The effect of vaccine formulations based on two GnRH analogue conjugates with KLH and containing various adjuvants was determined. The conjugates were prepared from equal amounts of one and ten cysteine replacement analogues at a conjugation ratio of between 7 and 10 in accordance with the procedures of Example 1. Six formulations were prepared with Alhydrogel, Alhydrogel with 20, 100 and 200 micrograms of Regressin per dose, essophor and regressin in oil. The formulations were administered in doses of 500 micrograms of conjugate at zero and 35 days. All the formulations were administered by IM injection to 5 bulls and 5 steers. Two of the bulls and three of the steers in each group had been involved in a previous unsuccessful trial and were somewhat more sensitized to the vaccination.

The effect was evaluated in terms of antibody titer against GnRH and suppression of testosterone production. Although only some adjuvant formulation developed significant titers all formulations were able to achieve a significant reduction in testosterone level in the bulls tested. Seven of the bulls failed to display a count of 10% of Iodine 125 counts possible at a 1:10 dilution including two previously treated bulls. The essophor formulation had the highest proportion of non responders (8 out of 10) including the two previously treated bulls and the one previously treated steer.

What is claimed is:

1. An agent capable of stimulating the immune system of a mammal to produce antibodies which bind to the mammal's native GnRH consisting essentially of a conjugate of
   (a) a GnRH molecule in which a single cysteine residue replaces an amino acid which normally occurs in GnRH decapeptide at the one, six or ten position and wherein the free amino or carboxyl group of cysteine is blocked, and
   (b) an immunostimulating protein carrier molecule.

2. The agent of claim 1 wherein the protein carrier molecule has a molecular weight in excess of about 15 kd.

3. The agent of claim 1 wherein the conjugate has a heterobifunctional linkage.

4. The agent of claim 1 wherein the ratio of GnRH molecule to the protein carrier molecule is between about 2 and 16 GnRH molecules per $10^5$ daltons of carrier.

5. A vaccine for inhibiting the reproductive capability of a mammal consisting essentially of the agent of claim 1 and an adjuvant.

6. The vaccine of claim 5 wherein the adjuvant is selected from the group consisting of aluminum hydroxide gel, water-in-oil emulsions and muramyl dipeptides.

7. A process for inhibiting the reproductive capability of a mammal by stimulating its immune system to produce antibodies which bind to its native GnRH comprising administering to a mammal a vaccine whose immunogen is a conjugate of claim 1.

8. The process of claim 7 wherein the vaccine is administered to the mammal parenterally.

9. The process of claim 8 wherein the vaccine is administered to the mammal on at least two occasions which are at least one week apart.

* * * * *